United States Patent [19]

Baatz et al.

[11] 4,070,405
[45] Jan. 24, 1978

[54] PROCESS FOR WORKING UP LIQUID COPPER-CONTAINING CATALYST WASTE FROM ISOMERIZATION REACTIONS OF DICHLOROBUTENE

[75] Inventors: Rolf Baatz, Dormagen; Gunter Beilstein, Straberg; Dieter Grenner, Dormagen; Wilfried Keller, Leverkusen; Dimitry Steinbach, Cologne, all of Germany

[73] Assignee: Bayer Aktiengesellschaft, Germany

[21] Appl. No.: 704,792

[22] Filed: July 13, 1976

[30] Foreign Application Priority Data

July 19, 1975 Germany .............................. 2532472

[51] Int. Cl.² .............................................. C07C 21/00
[52] U.S. Cl. ............................. 260/654 R; 260/438.1
[58] Field of Search ............. 260/438.1, 654 R, 654 S, 260/414; 423/42; 252/414

[56] References Cited

U.S. PATENT DOCUMENTS

| | | | |
|---|---|---|---|
| 2,150,349 | 3/1939 | van Peski et al. | 260/438.1 |
| 3,830,858 | 8/1974 | Brown et al. | 260/654 R |

FOREIGN PATENT DOCUMENTS 723,185 12/1965 Canada ............................ 260/654 R

*Primary Examiner*—O. R. Vertiz
*Assistant Examiner*—Brian E. Hearn
*Attorney, Agent, or Firm*—Connolly and Hutz

[57] ABSTRACT

Improved working up of the waste from an isomerization reaction of dichlorobutene by precipitating the copper catalyst used in said process by adding a polar solvent and removing the resulting precipitate by filtration.

9 Claims, 2 Drawing Figures

PROCESS FOR WORKING UP LIQUID COPPER-CONTAINING CATALYST WASTE FROM ISOMERIZATION REACTIONS OF DICHLOROBUTENE

The isomerisation of dichlorobutenes has been frequently described. The processes used on a commercial scale are without exception processes where isomerisation is carried out in substantially anhydrous organic-liquid phase in the presence of a copper complex. Preferred complex formers are quaternary ammonium salts (cf. German Offenlegungsschrift No. 2,248,668) or amine hydrochlorides (cf. German Auslegeschrift No. 1,950,971). Copper naphthenates, oleates and stearates, partly in combination with substituted urea compounds, are described in German Offenlegungsschrift No. 2,212,235.

The unsaturated nature of the dichlorobutenes intended for isomerisation, coupled with the need to work at elevated temperatures (in the range from 30° to 160° C according to the above-mentioned Offenlegungsschrift), result in the formation of generally high-boiling secondary products which accumulate in the reaction solution. Minimising the formation of the secondary products is one of the main objects of conventional processes. Accumulation of the secondary products means that part of the reaction solution has to be removed from the circuit, with the result that some Cu-catalyst is also taken out of the system at the same time.

The non-pollutive working up or destruction of the reaction solution removed from the system is difficult for the following reasons:

a. Copper oxide dust enters the smoke gases of incineration plants.
b. Copper salts enter the effluents of washing installations.
c. Safe dumping is not possible both on account of the corrosive effect and on account of the high vapour pressure of dichlorobutene.
d. the solution tends to decompose at elevated temperatures. This makes working up by distillation difficult.
e. With water, hydrochloric acid is eliminated from dichlorobutenes. The increased danger of corrosion which this involves and the contamination of effluent with copper and dichlorobutenes complicate working up processes in the presence of an aqueous phase.

Through the absence of a suitable working up process, the non-optimum destruction is accompanied by exhaust and effluent pollution. In addition, an uneconomic proportion of the product is lost as waste. Accordingly, the prior processes are attended by disadvantages which are very serious by today's standards.

The object of the present invention is to improve working up of the isomerisation waste characterised above with a view to recycling as large a proportion as possible of the dichlorobutene into the process and allowing unavoidable waste to accumulate in a form in which it is not difficult to eliminate.

According to the invention, this object is achieved by precipitating the copper complexes dissolved in dichlorobutene by adding an excess of an apolar solvent and removing by filtration the deposit formed.

Accordingly, the present invention provides a process for working up liquid copper-containing catalyst waste from isomerisation reactions of dichlorobutene, characterised by the fact that the dissolved copper complexes are precipitated by the addition of an apolar solvent and filtered off.

In another embodiment of the process, the filtrate may be further worked up by distillation. Thus, according to this embodiment it is possible both to reuse the apolar solvent recovered by distillation as precipitant and to recycle the dichlorobutadiene recovered into the isomerisation process.

Suitable apolar solvents are, for example, straight-chain, branched-chain, aliphatic, cycloaliphatic and/or aromatic hydrocarbons. The following compounds and their mixtures are mentioned in order to illustrate the term "hydrocarbon": petroleum ether, light petrol (for example boiling range 30° – 70° C), ligroin (for example boiling range 70° – 250° C); pentane, hexane, heptane, octane, nonane, decane, undecane, dodecane, tridecane, tetradecane, pentadecane, hexadecane, also the respective isomers; cyclopentane, cyclohexane, decalin; benzene, toluene and xylene.

The apolar solvent is added in quantities such that the copper complexes are completely or partly precipitated. The exact quantity required may readily be determined by any expert according to his particular needs. It is preferred to use from 1 to 50 times the quantity by weight, preferably from 2 to 20 times the quantity by weight and more especiallyfrom 5 to 10 times the quantity by weight of the apolar solvent, based on the copper-containing catalyst waste stream.

If the filtrate is to be further worked up by distillation, it is advisable not to exceed a sump temperature in the range from 30° to 300° C (calculated at normal pressure).

Suitable precipitation temperatures are in the range from 0° to 250° C, preferably in the range from 10° to 100° C and with particular preference in the range from 20° to 50° C.

BRIEF DESCRIPTION OF THE DRAWINGS

The process according to the invention is described in the following with reference to two Figures.

a. Batch-type embodiment (cf.

Figure 1:
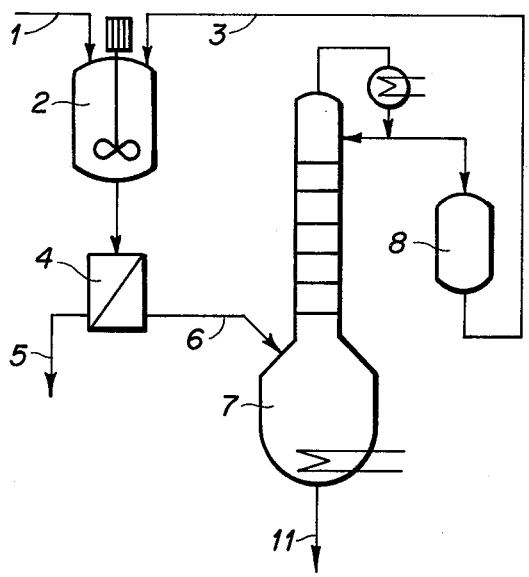
FIG. 1)

The waste stream 1 containing the copper complex is mixed with from 2 to 20 times the quantity of an apolar solvent 3 in a mixing vessel 2, which may be provided with a stirrer. A deposit is precipitated, containing substantially the total quantity of copper complex and by adsorption significant proportions of the high-boiling fractions present. The deposit it filtered off in a filter 4 and as a solid filter cake 5 is either dumped or treated to recover the copper present in it. The filtrate 6 is substantially free from copper. It is transferred into the still of a distillation column 7 and rectified. Virtually all the petroleum ether distils off overhead and is collected in the receiver 8 and introduced back into the precipitation vessel 2. Any fractions of dichlorobutene which may be present are harmless. In addition to dichlorobutenes, the distillation residue 11 contains higher-boiling compounds which, after recycling into the chloroprene process, are separated off from the dichlorobutenes and delivered to a suitable destruction plant. They only make up about 1 to 10% of the original quantity of waste and moreover are free from copper.

Continuous embodiment (cf. FIG. II):

The copper complex is precipitated from the waste stream 1 in the container 2 by means of an apolar solvent 3 in the same way as described above. The deposit 5 is discharged from a continuously operating filter 4 or from a filter battery designed to be operated in alternation. The filtrate 6 is delivered to the middle of a distillation column 7. The petroleum ether 3 which may be reused for precipitation is run off overhead from the distillation column 7. The high-boiling residue accumulates in the sump in admixture with dichlorobutenes 11 which are recovered after separation by distillation in the chloroprene process whilst the copper-free, high-boiling residue is removed and destroyed.

By means of the process according to the invention, it is possible to reduce the accumulation of residues to be destroyed from the copper-catalysed isomerisation of dichlorobutenes to between 1 and 10% of the original quantity and at the same time to free them from copper (copper content less than 5 ppm). This represents a significant contribution towards keeping air and water clean. The copper catalyst accumulates in a form in which it can be safely transported and subsequently used, for example for the production of copper. A significant economic advantage of the process according to the invention is the fact that most of the dichlorobutene present as solvent for the copper complex is recycled into the isomerisation process.

The invention is illustrated by the following Examples, in which the percentages quoted represent percentages by weight.

EXAMPLE 1

In the stirrer-equipped vessel 2 shown in FIG. 1, 5 kg of copper-containing isomerisation residue, consisting of 1.2% of copper (1) chloride and 1.5% of triethylamine in a dichlorobutene mixture were added at 25° C to 25 kg of petroleum ether (boiling range: 30° –50° C), and the suspension formed was filtered off through the filter 4. The filter residue weighed 0.40 kg and contained all the copper. 24.8 kg of petroleum ether were recovered from the copper-free filtrate by distillation in the column 7. In addition to 4.2 kg of dichlorobutenes, the residue left in the sump of the column contained 0.1 kg of higher boiling compounds (b.p. > 150° C).

EXAMPLE 2

Figure 2:
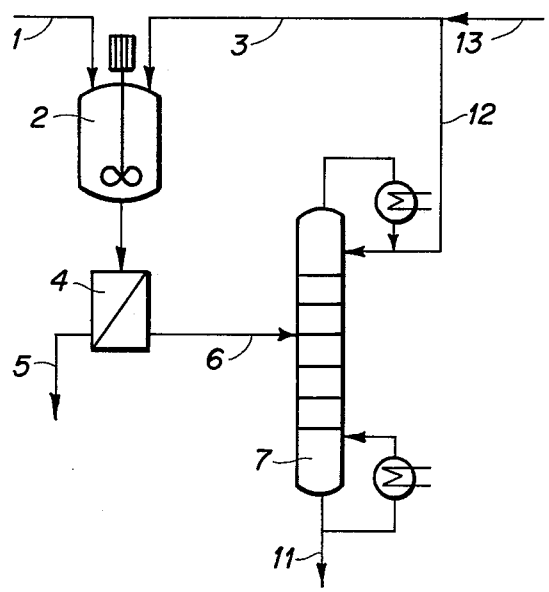

100 kg/hour of copper-containing isomerisation residue, consisting of 1.3% of copper (1) chloride and 2% of tri-n-propylamine in a dichlorobutene mixture, and 500 kg/h of light petrol (boiling range: 50° – 70° C) were introduced at 30° C into the precipitation apparatus 2 shown in FIG. 2. After filtration in the filter 4, the suspension formed was delivered to the continuously operating rectification column 7. The filter residue contained all the copper and was continuously removed from the filter (accumulation: 9 kg per hour).

The sump of the column was heated in such a way that 498 kg/h of light petrol distilled off from the column overhead and, made up with 10 kg/h of light petrol through the pipe 13 were returned to the filtration apparatus 2. 90 kg/h of a mixture of 85 kg of dichlorobutenes and 5 kg of relatively high boiling compounds (b.p. > 150° C) were removed from the sump of the column.

EXAMPLE 3

As in Example 1, 5 kg of copper-containing isomerisation residue, consisting of 2 % of copper (2) naphthenate and 1.9% of phenyl urea in admixture with dichlorobutenes were precipitated with 30 kg of n-heptane, followed by working up in the same way as in Example 1. The filter residue weighed 0.46 kg and contained all the copper. After distillation, the copper-free filtrate gave 29 kg of n-heptane. In addition to 4.1 kg of a dichlorobutene mixture, the column sump contained 0.12 kg of relatively high boiling compounds (b.p. > 150° C).

EXAMPLE 4

100 kg of copper-containing isomerisation residue with the same composition as in Example 1 were precipitated with 700 kg of petroleum ether (boiling range: 30° –50° C) as described in Example 2, followed by working up in the same way. 8.3 kg/h of filter residue which contained all the copper were discharged from the filter 4. 698 kg/h of petroleum ether were distilled off from the copper-free filtrate and, made up with 2 kg/h of fresh petroleum ether, were returned to the precipitation apparatus. 90 kg/h of a mixture of 83 kg of dichlorobutenes and 7 kg of high boiling compounds were run off from the sump of the column.

EXAMPLE 5

As in Example 1, 5 kg of isomerisation residue of 1.1% of copper (1) chloride and 7% of methyl urea in admixture with 60 parts of 1,4-dichloro-2-butene and 40 parts of 3,4-dichloro-1-butene, were precipitated with 40 kg of n-hexane followed by working up in the same way as described in Example 2. 0.42 g of solid residue were obtained. 39 kg of n-hexane were recovered from the copper-free filtrate. The distillation residue consisted of 4.0 kg of dichlorobutene mixture and 0.1 kg of high boiling compounds (b.p. > 150° C).

We claim:

1. A process for working up a liquid copper complex-containing catalyst waste stream from the isomerization reaction of dichlorobutene wherein the copper complex dissolved in dichlorobutene is precipitated at a temperature of from 0° to 250° C by the addition of an apolar solvent to the waste stream and said precipitated copper complex is recovered by filtration.

2. A process as claimed in claim 1, wherein the filtrate is worked up by distillation and the apolar solvent recovered is reused as precipitant.

3. A process as claimed in claim 2, wherein the dichlorobutene is recovered and is recycled into the isomerisation process.

4. a process as claimed in claims 1, wherein the apolar solvent is added to the copper-containing catalyst waste stream in 1 to 50 times the quantity by weight.

5. a process as claimed in claims 1, wherein the apolar solvent is added to the copper-containing catalyst waste stream in 2 to 20 times the quantity by weight.

6. A process as claimed in claims 1, wherein the apolar solvent is added to the copper-containing catalyst waste stream in 5 to 10 times the quantity by weight.

7. A process as claimed in claims 1, wherein straight-chain, branched, aliphatic, cycloaliphatic and/or aromatic hydrocarbons are used as the apolar solvent.

8. A process as claimed in claims 1, wherein the dissolved copper complexes are precipitated at temperatures of from 10° to 100° C.

9. a process as claimed in claims 1, wherein the dissolved copper complexes are precipitated at temperatures of from 20° to 50° C.

* * * * *